(12) United States Patent
Worrell et al.

(10) Patent No.: US 8,119,169 B2
(45) Date of Patent: Feb. 21, 2012

(54) OREGANO ORAL CARE COMPOSITIONS AND METHODS OF USE THEREOF

(75) Inventors: Cortney L. Worrell, Plainfield, NJ (US); Harsh M. Trivedi, Somerset, NJ (US); Kimberlee Panaligan, Parlin, NJ (US); Tao Xu, East Brunswick, NJ (US)

(73) Assignee: Colgate-Palmolive Company, New York, NY (US)

(*) Notice: Subject to any disclaimer, the term of this patent is extended or adjusted under 35 U.S.C. 154(b) by 0 days.

(21) Appl. No.: 11/256,788

(22) Filed: Oct. 24, 2005

(65) Prior Publication Data
US 2006/0140884 A1 Jun. 29, 2006

Related U.S. Application Data

(60) Provisional application No. 60/639,763, filed on Dec. 28, 2004.

(51) Int. Cl.
*A01N 65/00* (2009.01)

(52) U.S. Cl. ........................................... 424/725

(58) Field of Classification Search ........................ None
See application file for complete search history.

(56) References Cited

U.S. PATENT DOCUMENTS

| | | | |
|---|---|---|---|
| 4,454,163 A | 6/1984 | Gellman et al. | |
| 4,454,164 A | 6/1984 | Gellman et al. | |
| 4,808,400 A * | 2/1989 | Gaffar et al. | 424/52 |
| 5,000,943 A | 3/1991 | Scaglione et al. | |
| 5,368,844 A | 11/1994 | Gaffar et al. | |
| 5,405,836 A | 4/1995 | Richar et al. | |
| 5,416,075 A * | 5/1995 | Carson et al. | 514/23 |
| 5,723,500 A | 3/1998 | Stringer et al. | |
| 5,776,435 A | 7/1998 | Gaffar et al. | |
| 5,869,340 A * | 2/1999 | Shetty | 435/410 |
| 5,912,274 A | 6/1999 | Stringer et al. | |
| 5,955,086 A * | 9/1999 | DeLuca et al. | 424/745 |
| 5,980,869 A | 11/1999 | Sanker et al. | |
| 6,290,933 B1 | 9/2001 | Durga et al. | |
| 6,685,921 B2 | 2/2004 | Lawlor | |
| 2003/0206874 A1 | 11/2003 | Doyle et al. | |
| 2004/0253278 A1 | 12/2004 | Maxwell et al. | |

FOREIGN PATENT DOCUMENTS

| | | |
|---|---|---|
| EP | 0 321 180 | 6/1989 |
| EP | 0 528 457 | 2/1993 |
| FR | 2 618 670 | 2/1989 |
| JP | 57 056416 | 7/1982 |
| JP | 08 175947 | 7/1996 |
| JP | 2004-359634 | 12/2004 |
| WO | 9204884 A1 | 4/1992 |
| WO | WO 92/04884 | 4/1992 |
| WO | 2004019802 A2 | 3/2004 |
| WO | WO 2004/019802 | 3/2004 |

OTHER PUBLICATIONS

Natural News.com, 4 pages, 2008.*
Charai et al., "Chemical Composition and Antimicrobial Activities of Two Aromatic Plants: *Origanum marjorana*L. and *O. compactum* Benth.," J. Essent. Oil Res., 8:657-664, Nov./Dec. 1996.
Dorman et al., "Antimicrobial agents from plants: antibacterial activity of plant volatile oils," J. Applied Microbiology, 88:308-316, 2000.
Arcila-Lozano et al., 2004, "El Oregano: Propiedades, Composicion y Actividad Biologica de Sus Components," Arch. Latinoam. Nutr. 54(1):100-111, abstract only.
Didry et al., 1994, "Activity of Thymol, Carvacrol, Cinnamaldehyde and Eugenol on Oral Bacteria," Pharm. Acta Helv. 69(1):25-28.

* cited by examiner

*Primary Examiner* — Michael Meller
(74) *Attorney, Agent, or Firm* — Nikhil A. Heble

(57) ABSTRACT

A multi-benefit oral composition is provided. The oral composition is efficacious as an antibacterial, antiplaque, anti-inflammatory, anti-oxidant, and anti-halitosis oral composition. The active ingredient has one or more active compounds from an extract of oregano. The oral composition can be in the form of a mouth rinse; a dentifrice, including toothpaste, gels, powders; animal products; a film; or confectionaries, such as lozenges, and the like. Methods of making and using the oral composition are also provided.

3 Claims, No Drawings

OREGANO ORAL CARE COMPOSITIONS AND METHODS OF USE THEREOF

CROSS REFERENCE TO RELATED APPLICATION

This application claims the benefit of priority of U.S. Provisional Patent Application Ser. No. 60/639,763, filed Dec. 28, 2004.

BACKGROUND OF THE INVENTION

Human periodontal diseases are inflammatory disorders that are the result of complex interactions between periodontopathogens and the host's immune response. It is believed that there are two interrelated aspects to the progression of periodontal disease, the first is the activation of the immune system of the host and the second is the production of oxygen radicals and their related metabolites. Increased production of oxygen radicals may contribute to oxidative stress, which is believed to be involved in periodontal disease.

Gingivitis is the inflammation or infection of the gums and the alveolar bones that support the teeth. Gingivitis is generally believed to be caused by bacteria in the mouth (particularly the bacteria instigated in plaque formation) and the toxins formed as by-products from the bacteria. The plaque and bacterial toxins are believed to instigate oral tissue inflammation within the mouth. Periodontitis is a progressively worsened state of disease as compared to gingivitis, where the gums are inflamed and begin to recede from the teeth and pockets form in the recession, which ultimately may result in destruction of the bone and periodontal ligament. Thus, chronic infection and inflammation potentially results in the subsequent loss of teeth. Further, oral tissue inflammation can be caused by surgery, localized injury, trauma, or necrosis, or various systemic origins.

It is generally believed that the cellular components implicated by these diseases and conditions include epithelial tissue, gingival fibroblasts, and circulating leukocytes, all of which contribute to the host response to pathogenic factors generated by the bacteria. Thus, bacterial infection of the oral tissue ramps up the host's immune response and diminishes the healing process by generating free radical species (reactive oxygen species) and up-regulating inflammatory mediators that cause significant tissue damage.

Free radicals are atoms, ions, or molecules that contain an unpaired electron, and as such are usually unstable and exhibit short half-lives. Reactive oxygen species (ROS) are products produced during various biochemical processes, and include superoxide anions ($O_2^-$), hydrogen peroxide ($H_2O_2$), hydroxyl radicals ($OH^-$), and non-radical oxidants such as singlet oxygen ($^1O_2$). The formation of ROS can occur as part of many cellular processes including mitochondrial respiration, immune cell responses, cell injury, heat, radiation of many origins, from metabolism of drugs and other chemicals. The ROS are highly reactive and modify important cellular macromolecules. ROS initiate or accelerate disease processes.

In one example, ROS are generated during inflammation by phagocytic leukocytes, such as activated neutrophils that produce an "oxidative burst" of superoxide radicals, which are believed to be an essential factor in producing the cytotoxic effect of activated neutrophils. Moreover, superoxide may be produced physiologically by endothelial cells for reaction with nitric oxide, a physiological regulator, forming peroxynitrite, $ONOO^-$ which may decay and give rise to hydroxyl radical, OH. Additional sources of oxyradicals are "leakage" of electrons from disrupted mitochondrial or endoplasmic reticular electron transport chains, prostaglandin synthesis, oxidation of catecholamines, and platelet activation.

ROS are thought to be involved in almost all disease processes and the ageing process. Increased ROS formation under pathological conditions is believed to cause cellular damage through the action of these highly reactive molecules by crosslinking proteins, mutagenizing DNA, and peroxidizing lipids.

Another aspect of the immune response is the production of various intra and inter-cellular mediators of inflammation. One class of mediators extensively studied for their effect on the inflammatory response are the arachidonic acid metabolites namely prostaglandins and leukotrienes, that are produced through the cyclooxygenase or lipoxygenase enzyme pathways. These metabolites have been implicated as the prime mediators in gingivitis, periodontitis, osteomyelitis and other inflammatory diseases.

It would be desirable to have a method of treating a mammalian subject having infection, inflammation, and potential cellular damage in oral tissue, by killing the etiological pathogens of infection, reducing the production of one or more mediators of inflammation, and reducing free radical reactive oxygen species to reduce cellular damage to the oral tissue to promote healing.

BRIEF SUMMARY OF THE INVENTION

In an embodiment of the present invention, an oral care composition comprises an active ingredient comprising a safe and effective amount of one or more compounds from an extract of oregano, and an orally acceptable vehicle.

In another embodiment of the present invention, an anti-bacterial, anti-inflammatory, and antioxidant active ingredient for use in an oral care composition comprises a safe and effective amount of an extract of oregano.

In yet another embodiment, the present invention provides a method of providing one or more oral health benefits to an oral cavity of a mammalian subject. The method comprises preparing an oral care composition comprising an orally acceptable carrier; and a safe and effective amount of an active ingredient comprising one or more active compounds from an extract of oregano. The oral composition as prepared is contacted with one or more oral surfaces of the oral cavity to provide the benefits thereto.

It has been discovered that compositions and methods of this invention afford advantages over prior art antibacterial and antiplaque compositions, by providing an oral care composition for promoting multiple oral care benefits in a single active ingredient. The active ingredient comprises one or more active compounds from an extract of oregano. The active ingredient is highly effective against both gram-positive and gram-negative bacteria implicated in various conditions and diseases of the oral cavity. Additionally, the oral care composition provides anti-inflammatory and antioxidant effects to the oral cavity to promote healing and to reduce tissue damage and ageing. Further, the oral composition comprises an active ingredient that is natural and derived from a botanical source. Further uses, benefits and embodiments of the present invention are apparent from the description set forth herein.

DETAILED DESCRIPTION OF THE INVENTION

In accordance with the present invention, a highly efficacious antimicrobial, antioxidant, anti-inflammatory oral composition is provided that has a combination of one or more active compounds isolated from an extract of oregano.

The oral compositions of the present invention inhibit the growth of various oral bacteria that are implicated in forming plaque and causing oral diseases. The oral composition of the present invention is applied to one or more oral surfaces in the oral cavity, and promotes overall oral health, including inhibition of plaque formation, gingivitis, periodontitis, halitosis, and the like. For example, in an embodiment of the present invention, where an oral care composition comprises an orally acceptable delivery carrier and a safe and effective amount of the extract of oregano, it has been observed that the oregano extract has anti-inflammatory activity, antioxidant activity, and is highly efficacious against both gram-positive and anaerobic gram-negative bacteria, including those that form plaque and cause halitosis. Thus, the oral compositions of the present invention provide multiple oral care benefits simultaneously.

An additional advantage of the present invention is that the active antibacterial ingredients of various embodiments of the oral care composition are derived from botanicals that have been used as food for thousands of years. Such extracts are suitable as ingredients for daily use with an oral care hygiene product, such as dentifrice and mouth rinse formulations.

The compositions of the present invention comprise at least one active compound found in an extract of oregano. As referred to herein, such an "extract" of oregano is an extract obtained from dried leaves, cortex (i.e., bark), root, stalk, flower, or any suitable part of a plant from the Lamiaceae family, preferably of the genus *Origanum*. For example, suitable extracts include those from *Origanum vulgare* (commonly known as "oregano", "wild oregano", or "wild marjoram"), including its sub-species (*Origanum vulgare* ssp.), *Origanum onites* (commonly known as "Italian oregano" or "pot marjoram"), *Origanum majorana* (commonly known as "marjoram" or "sweet marjoram") and *Origanum heracleoticum*. *Origanum vulgare* subspecies include *O. vulgare* ssp. *vulgare*, *O. vulgare* ssp. *viride*, and *O. vulgare* ssp. *hirtum* (commonly known as "Greek oregano" or "Wild oregano"). As referred to hereinafter, "oregano" encompasses all suitable species and sub-species of the genus *Origanum*. The term "extract" also encompasses synthetic or semi-synthetic equivalents of such a natural extract or an active component thereof. In certain embodiments of the present invention, the active ingredient in the oral composition comprises one or more active compounds that have been isolated from an extract of oregano. In other embodiments, the active ingredient comprises an entire extract of oregano. It should be noted that certain oregano extracts are in lipophilic carriers, such as the case with essential oils, or where the extract is diluted in an oil carrier. Other extracts may be partially or fully separated from the lipophilic carriers and merely contain the active compounds of the extract and hydrophobic carriers or solvents. The extracts may be in liquid or dried powder forms. The terms "oregano extract" (which includes a form of the extract and at least one active compound) and one or more active compounds from an extract of oregano are used interchangeably herein.

In one embodiment, oregano extract is obtained from dried oregano leaves prepared by extracting the plant material using an appropriate solvent. Preferred solvents include methanol, ethanol, methylene chloride, hexane cyclohexane, pentane, petroleum ether, chloroform, ethylene dichloride, and hydrofluoroalkanes, such as 1,1,1,2-tetrafluoroethane (HFA-13A). Generally, one part of plant tissue (dry basis) is extracted with about 5 to about 50 parts, preferably about 15 parts to about 30 parts of solvent using an extraction apparatus where the solvent is contacted with the plant matter to obtain a concentrated paste which is then subjected to one or more additional extraction steps with different solvents to further concentrate the originally obtained paste over an extended period of time, preferably about 6 hours to about 1-2 days, more preferably for about 1 day.

Other methods of extraction include steam distillation or supercritical fluid extraction. In one embodiment of the present invention, the oregano extract is isolated by supercritical fluid extraction (SFE) using carbon dioxide ($CO_2$). Thus, in accordance with the present invention, oregano or active compounds from oregano are extracted from the oregano plant by any of a variety of suitable extraction methods known to one of skill in the art. Oregano is reported to contain over 30 compounds, such as carvarcrol, thymol, and rosmarinic acid.

While not limiting to any theories by which the present invention is bound, it is believed that carvacrol and thymol provide antimicrobial properties of extracts of oregano and rosmarinic acid provides anti-oxidant properties. However, as described above, over thirty active compounds have been identified in oregano extract, which represents a wide complement of compounds that contribute to efficacy in a variety of areas and functionality. The oral compositions of the present invention comprising an oregano extract active ingredient are effective as anti-inflammatory agents, as well.

"Inflammation" of the oral tissue generally refers to a localized protective response elicited by injury or destruction of tissues, which serves to destroy, dilute, or sequester both the injurious agent and the injured tissue. In the acute form, it is characterized by pain, heat, redness, swelling, and loss of function. Chronic inflammation is a slow process and primarily characterized by the formation of new connective tissue. Chronic inflammation is often a continuation of acute inflammation or a prolonged low-grade form of inflammation (such as that associated with periodontitis or gingivitis) and usually causes permanent tissue damage. Histologically, inflammation involves a complex series of events, including dilation of arterioles, capillaries, and venules, with increased permeability and blood flow; exudation of fluids, including plasma proteins, and leukocytic migration into the inflammatory locus. Inflammation corresponds to enhanced levels of pro-inflammatory cellular mediators, or substances that are released from cells, for example, as the result of the interaction of an antigen with an antibody or by the action of antigen with a sensitized lymphocyte.

In practice of the invention, the oral composition comprising oregano is applied to sites of inflamed oral tissue at a concentration that reduces the production of one or more inflammatory cellular mediators. In various embodiments of the present invention, the anti-inflammatory active ingredient of the oral composition simultaneously inhibits action and/or formation of multiple proinflammatory mediators, for example, both $PGE_2$ and TNF-α. Each respective mediator generally has a different mechanism in the pathogenesis of a disease.

In various embodiments, the oral compositions comprise oregano extract at a concentration where the production of one or more proinflammatory mediators, such as for example, $PGE_2$ is significantly diminished. However, as recognized by one of skill in the art, a complete suppression of formation of such cellular mediators is also potentially detrimental to the mammalian subject, and in accordance with certain embodiments of the present invention, the production of cytokines is not entirely repressed. Thus, in various embodiments, the oregano extract is present in the oral composition at a concentration that prevents the over-expression of one or more inflammatory mediators (which prevents an intrinsic mechanism for chronic disease), but still permits sufficient production of certain desirable mediator molecules (which are pleiotropic) to maintain homeostasis and normal cellular functions at basal levels.

In various embodiments, the oregano extract or one or more of its active compounds are used to prepare oral compositions of the present invention, such as, dentifrices, films, confectionaries, gels, and mouthrinses. Oral compositions may also be in the form of animal or pet care products in certain embodiments. The concentration of the active ingredient containing at least one active compound derived from an oregano extract depends upon the relative concentration of the active compounds present in the extract, or purity of the compounds, and as such, it is contemplated that the amount of oregano extract or active compounds present may vary as recognized by one of skill in the art. Additionally, the concentration of the active ingredients is typically dependent upon the form of the oral composition. For example, mouthrinses typically have a relatively low concentration of an active ingredient, as where dentifrices, gels, or toothpowders have a higher concentration to achieve the same delivered dosage based on ease of dispersion. Likewise, confectionary compositions typically have a relatively wide range of concentrations of active ingredient to enable sufficient dispersion as they dissolve or are masticated.

In one embodiment, an oral composition comprises a safe and effective amount of an active ingredient in an amount of about 0.0001 to about 10 weight %. In certain embodiments, the active ingredient is present in the oral composition at a concentration of about 0.001 to about 5%. In other embodiments, the active ingredient is present at about 0.01 to about 3%.

In various embodiments, an active ingredient comprising oregano is present in the oral composition. As described above, the active ingredient may comprise one or more active compounds isolated from an extract of oregano, as where in other embodiments the active ingredient contains the oregano extract or a derivative thereof that includes the one or more active ingredients. In one embodiment, an oral composition comprises an active ingredient having one or more active compounds (which may include embodiments where the active compound(s) are contained in an extract of oregano) present in the oral composition at a concentration of about 0.001 to about 3% by weight, more preferably about 0.01 to about 3%. In another embodiment, the one or more active compounds comprise less than 1% of the oral composition, and in certain embodiments are between about 0.001 to about 1% by weight. In other embodiments, the one or more active compounds comprises between about 0.01 and about 1% of the oral composition, and in other embodiments about 0.1 to about 0.5% of the oral composition.

In certain embodiments, the present invention provides oral care multiple oral care benefits to a mammalian subject and there may not be a need for additional active ingredients. In one such embodiment, an oral care composition comprises an active ingredient consisting essentially of one or more active compounds from an extract of oregano. In another embodiment, an oral care composition comprises an active ingredient consisting essentially of an extract of oregano.

In certain embodiments, an oral care composition of the present invention has an additional active agent ingredient in addition to the one or more active compounds from an oregano extract. If added, the additional active ingredients should not react with or detract from the efficacy and bioavailability of the oregano extract or any other ingredients of the composition, thus maintaining a stable and efficacious oral composition.

An optional active material is operable for the prevention or treatment of a condition or disorder of hard or soft tissue of the oral cavity, the prevention or treatment of a physiological disorder or condition, or to provide a cosmetic benefit. In various embodiments, the active is an "oral care active" operable to treat or prevent a disorder or provide a cosmetic benefit within the oral cavity (e.g., to the teeth, gingiva or other hard or soft tissue of the oral cavity). In other embodiments, the active is a "systemic active" which is operable to treat or prevent a disorder which, in whole or in part, is not a disorder of the oral cavity. Thus, compositions of the present invention may also be used for the treatment or prevention of systemic disorders, such as the improvement of overall systemic health characterized by a reduction in risk of development of systemic diseases, such as cardiovascular disease, stroke, diabetes, severe respiratory infection, premature and low birth weight infants (including associated post-partum dysfunction in neurologic/developmental function), and associated increased risk of mortality.

Optional oral care actives among those useful herein include whitening agents, anticaries agents, tartar control agents, periodontal actives, abrasives, breath freshening agents, malodour control agents, tooth desensitizers, salivary stimulants, anti-adhesion agents, plaque dispersing agents, and combinations thereof. It is understood that while general attributes of each of the above categories of actives may differ, there may be some common attributes and any given material may serve multiple purposes within two or more of such categories of actives.

In various embodiments, a highly efficacious antiplaque, antibacterial, and anti-inflammatory oral care composition contains an active ingredient comprising one or more active compounds from an oregano extract. However, in certain embodiments of the present invention, an additional antimicrobial/antibacterial ingredient may be included in the oral care compositions. If added, the antiplaque (e.g., antibacterial) active ingredients should not react with or detract from the efficacy and bioavailability of the oregano extract.

Suitable antibacterial agents for use in addition to the oregano extract of the present invention include other known antibacterial botanical extracts or active compounds isolated from such extracts. Non-limiting examples of antibacterial natural extracts include those isolated from green or oolong tea, gold thread, cranberry and other Ericaceae family plants, honeysuckle, grape seed, myrobalan, rosemary, east Indian walnut, neem, niruri, and pine bark.

Green tea and oolong tea are isolated from the *Camellia sinensis*. The active components are believed to be the polyphenol catechines including catechin, epocatechin, epigallocatechin, epicatchin gallate, gallocatechin and epigallocatechin. Gold thread extracts are obtained from one or more of the following plant families Annonaceae, Berberidaceae, Menispermaceae, Papaveraceae, Ranunculaceae, Rutaceae, Zingiberaceae, Nadina, Mahonia, *Thalictrum* spp. The active compound is believed to be berberine. The honeysuckle (*Lonicera ceprifolium*) extracts are obtained from the flower of the honeysuckle plant. The active polyphenol materials in the honeysuckle extract are believed to be the chlorogenic acid and/or lutenolin flavanoids. The Ericaceae family broadly refers to over 100 genera and the over 4,000 associated species, such as those disclosed in U.S. Pat. No. 5,980,869 to Sanker, et al. In certain embodiments, extracts from plants in the *Vaccinium* genus are useful as antibacterial natural extracts, such as cranberry (*Vaccinium macrocarpon*).

Other natural extracts that are known antimicrobial agents are those listed in the International Cosmetic Ingredient Dictionary and Handbook, Tenth Ed., 2004, including the following extracts. Grape seed is extracted from *Vitis Vinifera* seed. Myrobalan is preferably extracted from *Terminalia Bellerica* fruit. *Rosmarinus Officinalis* leaf is isolated to create rosemary extract. Pine bark extract is preferably extracted from the cortex (bark) of *Pinus Pinaster* (Maritime pine). The leaf of East Indian walnut (*Albizia Lebbek*) is used for the extract. The extract of the cortex of the neem or margosa plant (*Melia Azadirachta*) is a known antibacterial component. *Niruri* or *Phyllanthus Niruri* extract is also a known antibacterial extract.

Extracts suitable for use in the present invention can be obtained from any part of the plant including the leaf, stem, bark, pulp, seed, flesh, juice, root and mixtures thereof. It is preferred that the extract is obtained from the leaf, pulp and seed, more preferably from the leaf, flower or bark. The natural extracts containing antibacterial active compounds that are useful as additional antiplaque, e.g., antibacterial agents, in the oral compositions should be safe and suitable for use in mammals.

Other useful antimicrobial agents include non-ionic and anionic agents known to one of skill in the art. Examples of non-ionic agents include substantially water insoluble, non-cationic antibacterial agents. For example, such antibacterial agents include an alkylphenoxy phenol; a cycloalkyl-phenoxyphenol; a 9,10-dihydrophenanthrenol; an alkylphenol; a cycloalkyl-phenol; a phenolic compound; a halogenated carbanilide; a halogenated salicylanilide; a benzoic ester; a halogenated diphenyl ether, and mixtures thereof.

The nonionic antibacterial alkylphenoxy phenol or cycloalkyl-phenoxyphenol or -9,10-dihydrophenanthrenol includes a noncationic antibacterial phenol containing, relative to the hydroxyl group, an alkyl or cycloalkyl group, preferably tert-butyl (t-butyl), in 2-position, and substituents in one or both of the 4- and 5-positions, one of which may be phenyl or 2', 3' and/or 4' substituted alkyl or cycloalkyl phenyl, preferably 4'-t-butyl phenyl or a phenanthrene containing a hydroxyl substituent in the 2- or 3-position and alkyl or cycloalkyl, preferably t-butyl, substituents in the other of the 2- and 3-positions and in at least one of the other rings and are described in U.S. Pat. No. 5,723,500 to Stringer et al., issued Mar. 3, 1998.

The water insoluble non-ionic antibacterial alkyl-phenol or cycloalkyl-phenol include a phenol containing, relative to the hydroxyl group, an alkyl or cycloalkyl group, preferably tert-butyl (t-butyl), in the 2-position, and substituents in one or both of the 4- and 5-positions, one or both of which may be alkyl or cycloalkyl, one being preferably t-butyl, such as those described in U.S. Pat. No. 5,912,274, Stringer et al., Jun. 15, 1999.

The phenolic compounds among those useful herein include phenol and its homologs, mono and polyalkyl and aromatic halophenols, resorcinol and its derivatives, and bisphenolic compounds, such as those disclosed in U.S. Pat. No. 5,368,844, Gaffar et al., issued Nov. 29, 1994. Certain preferred phenolic compounds are n-hexyl resorcinol and 2,2'-methylene bis (4-chloro-6-bromophenol).

Exemplary halogenated carbanilides, halogenated salicylanilides and benzoic esters are disclosed in U.S. Pat. No. 5,776,435, Gaffar et al., issued Jul. 7, 1998. Halogenated carbanilides include 3,4,4'-trichlorocarbanilide, 3-trifluoromethyl-4,4'-dichlorocarbanilide, and 3,3',4-trichlorocarbanilide. Halogenated salicylanilides include 4'5-dibromosalicylanilide, 3,4',5-trichlorosalcylanilide, 3,4',5-tribromosalicylanilide, 2,3,3',5-tetrachlorosalicylanilide, 3,3',5-tetrachlorosalicylanilide, 3,5-dibromo-3'-trifluoromethyl salicylanilide, 5-n-octanoyl-3'-trifluoromethyl salicylanilide, 3,5-dibromo-4'-trifluoromethyl salicylanilide, 3,5-dibromo-3'-trifluoro methyl salicylanilide (Fluorophene), and mixtures thereof. Benzoic esters include methyl-p-hydroxybenzoic ester, ethyl-p-hydroxybenzoic ester, propyl-p-hydroxybenzoic ester, and butyl-p-hydroxybenzoic ester.

A particularly suitable non-ionic antiplaque antibacterial agent is a diphenyl ether selected from the group comprising 2,4,4'-trichloro-2'-hydroxydiphenyl ether (triclosan) and 2,2'-dihydroxy-5,5'-dibromodiphenyl ether. Triclosan is particularly suitable for use as an additional antiplaque antibacterial agent.

In various embodiments, the additional antiplaque antibacterial agents added to the oral composition of the present invention comprise about 0.0001% to about 10%, preferably about 0.001% to about 5%, more preferably about 0.01% to about 3%, depending on the concentration of the active compounds and the form of the oral composition.

The oral composition of the present invention may contain an anticaries agent, such as a fluoride ion source or a fluorine-providing component. In various embodiments, the fluoride based anticaries agent is present in an amount sufficient to supply about 25 ppm to 5,000 ppm of fluoride ions. Useful anticaries agents include inorganic fluoride salts, such as soluble alkali metal salts. For example, preferred fluoride sources useful in the oral composition are sodium fluoride, potassium fluoride, sodium fluorosilicate, ammonium fluorosilicate, sodium monfluorophosphate (MFP), and amine fluorides, including olaflur (N'-octadecyltrimethylendiamine-N,N,N'-tris(2-ethanol)-dihydrofluoride). Tin based compounds, including stannous fluoride and stannous chloride are also useful herein. In certain embodiments, sodium fluoride, sodium MFP, or olaflur (N'-octadecyltrimethylendiamine-N,N,N'-tris(2-ethanol)-dihydrofluoride). is preferred as an anticaries ingredient.

Where sodium fluoride is the sole fluoride-releasing salt present, illustratively an amount of about 0.01% to about 5%, about 0.05% to about 1% or about 0.1% to about 0.5%, sodium fluoride by weight is present in the composition.

In various embodiments, the oral compositions of the present invention comprise antitartar agents to prevent and/or minimize calculus formation. One or more of such agents can be present.

Suitable anticalculus agents include without limitation: phosphates and polyphosphates. Phosphate and polyphosphate salts are generally employed in the form of their wholly or partially neutralized water soluble cationic species (e.g., potassium, sodium or ammonium salts, and any mixtures thereof). Thus, useful inorganic phosphate and polyphosphate salts illustratively include monovalent cations with monobasic, dibasic and tribasic phosphates; tripolyphosphate and tetrapolyphosphate; mono-, di-, tri- and tetra-pyrophosphates; and cyclophosphates (also generally known in the art as "metaphosphates"). Useful monovalent cations of such phosphate salts include hydrogen, monovalent metals including alkali metals, and ammonium, for example.

Examples of useful antitartar agents include $Na_5P_3O_{10}$ (sodium tripolyphosphate or STPP), tetraalkali metal pyrophosphate salts such as $Na_4P_2O_7$ (tetrasodium pyrophosphate or TSPP), $K_4P_2O_7$ (tetrapotassium pyrophosphate), $Na_2K_2P_2O_7$ (disodium dipotassium pyrophosphate), $Na_2H_2P_2O_7$ (disodium dihydrogen pyrophosphate) and $K_2H_2P_2O_7$ (dipotassium dihydrogen pyrophosphate). Cyclophosphates, which are generally referred to as "metaphosphates", are cyclic phosphate anion compounds. Those useful as tartar control agents include, sodium hexametaphosphate and sodium trimetaphosphate, for example. In one embodiment, the active anticalculus system comprises sodium tripolyphosphate (STPP) and/or tetrasodium pyrophosphate (TSPP).

Other suitable tartar control agents include polyaminopropanesulfonic acid (AMPS), zinc citrate trihydrate, polypeptides such as polyaspartic and polyglutamic acids, polyolefin sulfonates, polyolefin phosphates, diphosphonates such as azacycloalkane-2,2-diphosphonates (e.g., azacycloheptane-2,2-diphosphonic acid), N-methyl azacyclopentane-2,3-diphosphonic acid, ethane-1-hydroxy-1,1-diphosphonic acid (EHDP) and ethane-1-amino-1,1-diphosphonate, phosphonoalkane carboxylic acids and salts of any of these agents, for example their alkali metal and ammonium salts.

In various embodiments where the anticalculus/anti-tartar active ingredients are present in the oral compositions, they range in concentration about 0.01 to about 10% by weight, more preferably between about 1 to about 5% by weight.

Additionally, various embodiments of the present invention include an anticalculus system that further comprises a synthetic anionic linear polycarboxylate polymer. Synthetic anionic polycarboxylates may also be used in the dentifrice compositions of the present invention as an efficacy enhancing agent for tartar control agents, as well as for a variety of other active ingredients. The anionic linear polycarboxylate is generally synthesized by using an olefinically or ethylenically unsaturated carboxylic acid that contains an activated carbon-to-carbon olefinic double bond and at least one carboxyl group. The acid contains an olefinic double bond which readily functions in polymerization because of its presence in the monomer molecule either in the alpha-beta position with respect to a carboxyl group or as part of a terminal methylene grouping. Illustrative of such acids are acrylic, methacrylic, ethacrylic, alpha-chloroacrylic, crotonic, beta-acryloxy propionic, sorbic, alpha-chlorsorbic, cinnamic, beta-styrilacrylic, muconic, itaconic, citraconic, mesaconic, glutaconic, aconitic, alpha-phenylacrylic, 2-benzyl acrylic, 2-cyclohexylacrylic, angelic, umbellic, fumaric, maleic acids and anhydrides. Other olefinic monomers copolymerizable with such carboxylic monomers include vinyl acetate, vinyl chloride, dimethyl maleate and the like. The synthetic anionic linear polymeric polycarboxylate component is mainly a hydrocarbon with optional halogen and O-containing substituents and linkages as present in for example ester, ether and OH groups. The copolymers preferably contain sufficient carboxylic salt groups for water-solubility. The terms "synthetic" and "linear" do not include known thickening or gelling agents comprising carboxymethylcellulose and other derivatives of cellulose and natural gums, nor Carbopols having reduced solubility due to cross-linkages.

Preferred are 1:4 to 4:1 copolymers of maleic anhydride or acid with another polymerizable ethylenically unsaturated monomer, preferably methyl vinyl ether (methoxyethylene) having a molecular weight (M.W.) of about 30,000 to about 2,500,000. These copolymers are commercially available, for example as GANTREZ® AN-139 (M.W. 1,000,000), AN-119 (M.W. 200,000) and S-97 Solution (M.W. 1,500,000), from ISP Corporation.

In various embodiments, where the anti-tartar/anticalculus system comprises a synthetic anionic polycarboxylate, it is preferably present about 0.001 to about 5 weight %. In another embodiment, the synthetic anionic polycarboxylate is present about 0.01 to about 1.5 weight %, most preferably at about 1 weight % of the oral care composition. In one embodiment according to the present invention, the anticalculus system comprises a copolymer of maleic anhydride and methyl vinyl ether, such as for example, the GANTREZ® S-97 product discussed above. In one embodiment, the antitartar active ingredient system of the oral care composition comprises TSPP at about 0.5 to about 1.5% by weight, STPP at about 1 to about 10% by weight, and a copolymer of maleic anhydride and methyl vinyl ether at about 0.5 to about 1.5% by weight.

In another embodiment the oral composition comprises an orally acceptable stannous ion source useful, for example, in helping reduce gingivitis, plaque, calculus, caries or sensitivity. One or more such sources can be present. Suitable stannous ion sources include without limitation stannous fluoride, other stannous halides such as stannous chloride dihydrate, stannous pyrophosphate, organic stannous carboxylate salts such as stannous formate, acetate, gluconate, lactate, tartrate, oxalate, malonate and citrate, stannous ethylene glyoxide and the like. One or more stannous ion sources are optionally and illustratively present in a total amount of about 0.001% to about 10%, for example about 0.1% to about 7% or about 1% to about 5% by weight of the composition.

In another embodiment the oral composition comprises an orally acceptable zinc ion source useful, for example, as an antimicrobial, anticalculus or breath-freshening agent. One or more such sources can be present. Suitable zinc ion sources include without limitation zinc acetate, zinc citrate, zinc gluconate, zinc glycinate, zinc oxide, zinc sulfate, sodium zinc citrate and the like. One or more zinc ion sources are optionally and illustratively present in a total amount of about 0.001% to about 3%, for example about 0.1% to about 1%, by weight of the composition.

In another embodiment the composition comprises an orally acceptable sialagogue (saliva stimulating agent) useful for example in amelioration of dry mouth. One or more of such agents can be present in a saliva stimulating effective total amount. Suitable sialagogues include without limitation food acids such as citric, lactic, malic, succinic, ascorbic, adipic, fumaric and tartaric acids.

In another embodiment the composition comprises an orally acceptable breath-freshening agent. One or more such agents can be present in a breath-freshening effective total amount. Suitable breath-freshening agents include without limitation zinc salts such as zinc gluconate, zinc citrate and zinc chlorite, $\alpha$-ionone and the like.

In addition to the above described antibacterial agents, which are optionally added to the oral compositions of the present invention, and preferably prevent plaque formation, another embodiment of the composition comprises an orally acceptable antiplaque agent. An antiplaque agent can operate by an anti-adhesion mechanism, plaque disrupting mechanism, or both. One or more such agents can be present in an antiplaque effective total amount. Additional suitable antiplaque agents include without limitation stannous, copper, magnesium and strontium salts, dimethicone copolyols such as cetyl dimethicone copolyol, papain, glucoamylase, glucose oxidase, urea, calcium lactate, calcium glycerophosphate, strontium polyacrylates and chelating agents such as citric and tartaric acids and alkali metal salts thereof.

In another embodiment the composition comprises an orally acceptable anti-inflammatory agent other than the oregano compounds as described above. One or more such agents can be present in an anti-inflammatory effective total amount. Suitable anti-inflammatory agents include without limitation steroidal agents such as flucinolone and hydrocortisone, and nonsteroidal agents (NTHEs) such as ketorolac, flurbiprofen, ibuprofen, naproxen, indomethacin, diclofenac, etodolac, indomethacin, sulindac, tolmetin, ketoprofen, fenoprofen, piroxicam, nabumetone, aspirin, diflunisal, meclofenamate, mefenamic acid, oxyphenbutazone and phenylbutazone. One or more anti-inflammatory agents are optionally present in the composition in an anti-inflammatory effective amount.

In various embodiments, the orally acceptable dentifrice carrier used to prepare an oral composition comprises a water-phase. As recognized by one of skill in the art, the oral compositions of the present invention optionally include other materials, such as for example, viscosity modifiers, diluents, surface active agents, such as surfactants, emulsifiers, and foam modulators, pH modifying agents, abrasives, humectants, emollients, and moisturizers, mouth feel agents, sweetening agents, flavor agents, colorants, preservatives and combinations thereof. It is understood that while general attributes of each of the above categories of materials may differ, there may be some common attributes and any given material may serve multiple purposes within two or more of such categories of materials. Preferably, such carrier materials are selected for compatibility with the active ingredient comprising an extract of oregano, as well as with other ingredients of the composition.

In various embodiments, the present invention provides a method of promoting oral health in an oral cavity and for treating plaque on an oral surface (tooth surface) of a mammalian subject. In one embodiment a method of providing one or more oral health benefits to an oral cavity of a mammalian subject entails preparing an oral care composition comprising an orally acceptable carrier and a safe and effective amount of an active ingredient comprising one or more active compounds from an extract of oregano. The prepared oral composition is contacted with an oral surface of the oral cavity. The oral composition of the present invention containing the active ingredient comprising an extract of oregano provides multiple oral health benefits including antigingivitis, anti-periodontitis, anti-inflammatory, anti-aging, breath freshening, and combinations thereof. For example, in certain embodiments of the present invention, contacting the oral composition with the oral surface reduces inflammation of the oral tissue. This anti-inflammatory effect can occur by the anti-oxidant properties of the oregano extract which are believed to prevent oxyradical-induced damage by scavenging free radical compounds (ROS) after they have been formed in the oral cavity; by reducing one or more mediators of inflammation in the inflamed tissue in the oral cavity, or by both mechanisms. The present invention also provides an antimicrobial effect when the oral composition comprising oregano extract contacts an oral surface. The active ingredient comprising an oregano extract is efficacious against Gram negative and Gram positive oral bacteria, both of which are implicated in halitosis, plaque formation, and chronic oral disease, such as gingivitis and periodontitis. Thus, the present invention is an efficacious antibacterial agent.

Additionally, the contacting of the oral tissue with the oral composition comprising an extract of oregano serves to reduce or improve one or more conditions selected from the group consisting of: plaque formation, halitosis, gingivitis, and periodontitis.

Thus, in various embodiments of the present invention, the oral care composition that is prepared as a dentifrice, confectionary, film, mouthwash, or animal product. The oral composition is preferably contacted with or applied regularly to an oral surface, preferably on a daily basis, at least one time daily for multiple days, but alternately every second or third day. Most preferably the oral composition is applied to the oral surfaces from 1 to 3 times daily, at a pH of about 4.5 to about 10, generally about 5.5 to about 8, preferably about 6 to 8, for at least 2 weeks up to 8 weeks or more up to lifetime.

The oral compositions of the present invention may be prepared by suitably mixing the ingredients. For instance, in the preparation of a mouthrinse, the antibacterial active ingredient comprising oregano extract is dispersed in a flavor oil or an alcohol and then added to a mixture of humectants, surfactants, and water. The resulting rinse product is then packaged. Dentifrices are prepared by adding various salts (including fluoride), and sweeteners (e.g., saccharin) to water, where it is mixed. Into another container, all humectants, gums, and polymers are added together. The water mixture described above is added to the container with the humectants, gums, and polymers. The combined ingredients are optionally heated to about 140° to about 160° F. to disperse the gums and polymers. The heated mixture is then cooled to less than approximately 100° F. The mixture is then combined with abrasives, where it is mixed at high speed under a vacuum for 15 to 20 minutes. The flavor oil (and/or alcohol) and active ingredient is then added to the mixture and mixed under high speed and vacuum until sufficiently dispersed. The surfactant(s) are added and the mixture is again mixed to disperse.

The oral composition of this invention can be incorporated into confectionary and tropes. Such methods of forming confectionary (e.g., gum) or tropes (e.g., lozenges) are well known by one of skill in the art, and can be prepared by stirring the extracts into a warm gum base or coating the outer surface of a gum base (for example, jelutone, rubber latex, vinylite resins, inter alia), desirably with conventional plasticizers or softeners, sugar or other sweeteners or carbohydrates such as glucose, sorbitol and the like.

Where the oral composition is in the form of a film, it can be formed by any number of conventional film forming processes, such as conventional extrusion or solvent casting processes. For example, to prepare a film by solvent casting, a film forming polymer is dissolved in a sufficient amount of a solvent which is compatible with the polymer. After a solution has been formed, a plasticizer can be added with stirring, and heat can be applied if necessary to aid dissolution, until a clear and homogeneous solution has been formed, followed by the addition of the active ingredients, surface active agents, bulking agents, and any other ingredients such as flavors and sweeteners. For ease of use, the dry film can be cut into pieces of suitable size and shape and packed into a suitable container.

The following Examples further illustrate the present invention, but it is understood that the invention is not limited thereto. All amounts and proportions referred to herein and in the appended claims are by weight unless otherwise indicated.

EXAMPLE I

A dentifrice formulation is prepared containing a powdered extract of oregano active ingredient extracted from *Origanum vulgare* available from Cedarville was provided at 0.3%. Further, additional active tartar control active ingredients were added containing tetrasodium pyrophosphate (TSPP), sodium tripolyphosphate (STPP). A copolymer of maleic anhydride and methyl vinyl ether (GANTREZ® S97 liquid) was also added with the ingredients listed in Table I.

A dentifrice composition having the ingredients listed in Table I is prepared by the following method. Sodium saccharin, sodium monofluorophosphate, tetrasodium pyrophosphate (TSPP), sodium tripolyphosphate (STPP) and any other salts are dispersed in water and mixed in a conventional mixer under agitation. The humectants e.g., glycerin and sorbitol, are added to the water mixture under agitation. Then organic thickeners, such as carageenan, and any polymers, such as GANTREZ®, are added. The resultant mixture is agitated and heated to approximately 140° to 160° F. until a homogeneous gel phase is formed, and then cooled. A pigment such as TiO$_2$ is added into the gel phase, colorant, and any acid or base (e.g., NaOH) required to adjust the pH to 6 to 7. The mixture is then transferred to a high-speed vacuum mixer; where silica abrasive SYLODENT® XWA 650, SYLODENT® 783, and silica thickener ZEODENT® 165 are added. The mixture is then mixed at high speed for from 5 to 30 minutes, under vacuum of about 20 to 50 mm of Hg, preferably about 30 mm Hg. The flavor oil and oregano extract are added and then mixed. Lastly, surfactants, such as sodium lauryl sulfate (SLS) are added into the mixer. The resultant product is a homogeneous, semi-solid, extrudable paste or gel product.

TABLE I

| Ingredient | Final Wt. % |
| --- | --- |
| Oregano Extract | 0.3 |
| TSPP | 1.0 |
| STPP | 7.0 |
| GANTREZ ® S97—liquid solution | 1.0 |
| Sorbitol | 18.7 |
| Glycerin | 12.0 |
| Sodium fluoride | 0.243 |
| Sodium saccharin | 0.3 |
| Sodium hydroxide | 1.0 |
| CMC 2000S | 0.8 |
| Carrageenan | 0.4 |
| SYLODENT ® 783 | 11.0 |
| SYLODENT ® XWA 650 | 10.0 |

TABLE I-continued

| Ingredient | Final Wt. % |
| --- | --- |
| ZEODENT ® 165 | 3.5 |
| Sodium lauryl sulfate | 1.2 |
| TiO$_2$ coated Mica | 0.1 |
| Flavor (89-332) | 1.0 |
| Blue Color Solution | 0.05 |
| Water | Q.S. |

What is claimed is:

1. An oral care composition consisting essentially of:
    a) a compound selected from the group consisting of isolated carvacrol and isolated rosmarinic acid present at about 0.001 to about 10% by weight of the composition;
    b) a compound selected from the group consisting of a phosphate salt and a polyphosphate salt;
    c) a compound selected from the group consisting of triclosan and a zinc salt;
    d) a synthetic anionic linear polycarboxylate polymer which is a 1:4 to 4:1 copolymer of maleic anhydride or acid with another polymerizable ethylenically unsaturated monomer; and
    e) an orally acceptable carrier.

2. The composition of claim 1 wherein the compound in a) is present at about 0.01 to about 5% by weight of the composition.

3. The composition of claim 1 wherein the compound in a) is present at about 0.01 to about 3% by weight of the composition.

* * * * *